US010159490B2

(12) United States Patent
Wallace et al.

(10) Patent No.: US 10,159,490 B2
(45) Date of Patent: Dec. 25, 2018

(54) VASO-OCCLUSIVE DEVICES

(71) Applicant: STRYKER EUROPEAN HOLDINGS I, LLC, Kalamazoo, MI (US)

(72) Inventors: Michael P. Wallace, Pleasanton, CA (US); E. Skott Greenhalgh, Gladwyne, PA (US)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 240 days.

(21) Appl. No.: 15/148,872

(22) Filed: May 6, 2016

(65) Prior Publication Data

US 2016/0324668 A1    Nov. 10, 2016

Related U.S. Application Data

(60) Provisional application No. 62/159,154, filed on May 8, 2015.

(51) Int. Cl.
*A61F 2/06* (2013.01)
*A61B 17/12* (2006.01)
(Continued)

(52) U.S. Cl.
CPC .... *A61B 17/12172* (2013.01); *A61B 17/1214* (2013.01); *A61B 17/1215* (2013.01);
(Continued)

(58) Field of Classification Search
CPC ............ A61B 17/1214; A61B 17/1215; A61B 17/12109; A61B 17/12113; A61F 2/90;
(Continued)

(56) References Cited

U.S. PATENT DOCUMENTS 4,754,685 A    7/1988  Kite et al.
4,820,298 A    4/1989  Leveen et al.
(Continued)

FOREIGN PATENT DOCUMENTS

CN    102368963 A    3/2012
WO    99/39646 A1    8/1999
(Continued)

OTHER PUBLICATIONS

Notification of the First Office Action for Chinese Patent Application No. 201580027802.4, dated Sep. 29, 2017, Applicant Stryker European Holdings I, LLC, in Chinese language with translation provided by foreign associate, 17 pages.
(Continued)

*Primary Examiner* — Tuan V Nguyen
(74) *Attorney, Agent, or Firm* — Vista IP Law Group LLP

(57) ABSTRACT

A vaso-occlusion system for occluding an aneurysm includes a delivery catheter having a delivery lumen extending therethrough, a pusher member at least partially extending through the delivery lumen, and a vaso-occlusive device loaded within the delivery lumen, the vaso-occlusive device comprising an expandable braid formed out of a plurality of elongate braid filaments, the elongate braid elements having respective proximal end portions that are formed into a flexible transition section having a proximal end portion attached to a distal end of the pusher member and/or to an elongate central member coupled to, and extending distally of, the pusher member.

16 Claims, 5 Drawing Sheets

(51) Int. Cl.
*A61F 2/90* (2013.01)
*A61F 2/844* (2013.01)
*A61F 2/966* (2013.01)
*A61F 2/82* (2013.01)
*A61F 2/95* (2013.01)

(52) U.S. Cl.
CPC .. *A61B 17/12031* (2013.01); *A61B 17/12109* (2013.01); *A61B 17/12113* (2013.01); *A61F 2/844* (2013.01); *A61F 2/90* (2013.01); *A61F 2/966* (2013.01); *A61B 2017/12054* (2013.01); *A61F 2002/823* (2013.01); *A61F 2002/9511* (2013.01)

(58) Field of Classification Search
CPC .... A61F 2/844; A61F 2/966; A61F 2002/823; A61F 2/12172
See application file for complete search history.

(56) References Cited

U.S. PATENT DOCUMENTS

| | | | |
|---|---|---|---|
| 4,870,887 A | 10/1989 | Tresslar et al. | |
| 4,994,069 A | 2/1991 | Ritchart et al. | |
| 5,186,992 A | 2/1993 | Kite | |
| 5,217,484 A | 6/1993 | Marks | |
| 5,304,194 A | 4/1994 | Chee et al. | |
| 5,382,259 A | 1/1995 | Phelps et al. | |
| 5,423,849 A | 6/1995 | Engelson et al. | |
| 5,536,274 A | 7/1996 | Neuss | |
| 5,639,277 A | 6/1997 | Mariant et al. | |
| 5,690,666 A | 11/1997 | Berenstein et al. | |
| 5,690,667 A | 11/1997 | Gia | |
| 5,792,157 A | 8/1998 | Mische et al. | |
| 5,888,201 A | 3/1999 | Stinson et al. | |
| 5,891,191 A | 4/1999 | Stinson | |
| 5,964,797 A | 10/1999 | Ho | |
| 5,976,162 A | 11/1999 | Doan et al. | |
| 6,019,786 A | 2/2000 | Thompson | |
| 6,024,754 A | 2/2000 | Engelson | |
| 6,066,158 A | 5/2000 | Engelson et al. | |
| 6,096,052 A | 8/2000 | Callister et al. | |
| 6,165,178 A | 12/2000 | Bashiri et al. | |
| 6,187,027 B1 | 2/2001 | Mariant et al. | |
| 6,193,728 B1 | 2/2001 | Ken et al. | |
| 6,203,547 B1 | 3/2001 | Nguyen et al. | |
| 6,238,403 B1 | 5/2001 | Green, Jr. et al. | |
| 6,254,592 B1 | 7/2001 | Samson et al. | |
| 6,287,318 B1 | 9/2001 | Villar et al. | |
| 6,350,270 B1 | 2/2002 | Roue | |
| 6,361,545 B1 | 3/2002 | Macoviak et al. | |
| 6,458,119 B1 | 10/2002 | Berenstein et al. | |
| 6,475,227 B2 | 11/2002 | Burke et al. | |
| 6,551,340 B1 | 4/2003 | Konya et al. | |
| 6,589,256 B2 | 7/2003 | Forber | |
| 6,592,617 B2 | 7/2003 | Thompson | |
| 6,632,241 B1 | 10/2003 | Hancock et al. | |
| 6,660,020 B2 | 12/2003 | Wallace et al. | |
| 6,682,546 B2 | 1/2004 | Amplatz | |
| 6,860,893 B2 | 3/2005 | Wallace et al. | |
| 6,866,677 B2 | 3/2005 | Douk et al. | |
| 6,872,218 B2 | 3/2005 | Ferrera et al. | |
| 6,984,240 B1 | 1/2006 | Ken et al. | |
| 6,994,689 B1 | 2/2006 | Zadno Azizi et al. | |
| 7,066,946 B2 | 6/2006 | Douk et al. | |
| 7,128,752 B2 | 10/2006 | Bales | |
| 7,323,001 B2 | 1/2008 | Clubb et al. | |
| 7,326,225 B2 | 2/2008 | Fererra et al. | |
| 7,749,242 B2 | 7/2010 | Tran et al. | |
| 7,828,816 B2 | 11/2010 | Mazzocchi et al. | |
| 7,879,062 B2 | 2/2011 | Galdonik et al. | |
| 8,002,789 B2 | 8/2011 | Ramzipoor et al. | |
| 8,016,852 B2 | 9/2011 | Ho et al. | |
| RE43,311 E | 4/2012 | Wallace et al. | |
| 8,172,862 B2 | 5/2012 | Wallace et al. | |
| 8,182,506 B2 | 5/2012 | Fitz et al. | |
| 8,361,138 B2 | 1/2013 | Adams | |
| 8,444,668 B2 | 5/2013 | Jones et al. | |
| 8,486,104 B2 | 7/2013 | Samson et al. | |
| 8,603,128 B2 | 12/2013 | Greene et al. | |
| 8,715,316 B1 | 5/2014 | Janardhan et al. | |
| 8,777,974 B2 | 7/2014 | Amplatz et al. | |
| 9,011,482 B2 | 4/2015 | Wallace et al. | |
| 9,060,777 B1 | 6/2015 | Wallace et al. | |
| 9,211,396 B2 | 12/2015 | Aboytes | |
| 2003/0093111 A1 | 5/2003 | Ken et al. | |
| 2004/0098023 A1 | 5/2004 | Lee et al. | |
| 2005/0222605 A1 | 10/2005 | Greenhalgh et al. | |
| 2005/0267510 A1 | 12/2005 | Razack | |
| 2005/0277978 A1 | 12/2005 | Greenhalgh | |
| 2006/0009799 A1 | 1/2006 | Kleshinski et al. | |
| 2006/0030876 A1 | 2/2006 | Peacock et al. | |
| 2006/0116709 A1 | 6/2006 | Sepetka et al. | |
| 2006/0116713 A1 | 6/2006 | Sepetka et al. | |
| 2007/0233186 A1 | 10/2007 | Meng | |
| 2008/0097401 A1 | 4/2008 | Trapp et al. | |
| 2008/0109057 A1 | 5/2008 | Calabria et al. | |
| 2009/0105748 A1 | 4/2009 | Fogarty et al. | |
| 2009/0112251 A1 | 4/2009 | Qian et al. | |
| 2009/0210047 A1 | 8/2009 | Amplatz et al. | |
| 2009/0266366 A1 | 10/2009 | Swann et al. | |
| 2009/0297582 A1 | 12/2009 | Meyer et al. | |
| 2010/0063578 A1 | 3/2010 | Ren et al. | |
| 2010/0152766 A1 | 6/2010 | Dieck et al. | |
| 2010/0228278 A1 | 9/2010 | Tran et al. | |
| 2011/0213405 A1 | 9/2011 | Porter et al. | |
| 2012/0158034 A1 | 6/2012 | Wilson et al. | |
| 2013/0112070 A1 | 5/2013 | Mach | |
| 2013/0116722 A1 | 5/2013 | Aboytes et al. | |
| 2013/0253572 A1 | 9/2013 | Molaei et al. | |
| 2013/0267992 A1 | 10/2013 | Tran et al. | |
| 2013/0274849 A1 | 10/2013 | Zaver et al. | |
| 2014/0135810 A1 | 5/2014 | Divino et al. | |
| 2014/0135827 A1 | 5/2014 | Amplatz et al. | |
| 2014/0277099 A1 | 9/2014 | Wallace et al. | |
| 2014/0330299 A1 | 11/2014 | Rosenbluth et al. | |
| 2015/0343181 A1* | 12/2015 | Bradway | A61B 17/12031 604/103.1 |

FOREIGN PATENT DOCUMENTS

| | | |
|---|---|---|
| WO | 03/082363 A1 | 10/2003 |
| WO | 2004/045425 A1 | 6/2004 |
| WO | 2005/065556 | 7/2005 |
| WO | 2007/041624 A1 | 4/2007 |
| WO | 2007/123638 A1 | 11/2007 |
| WO | WO 2010135352 A1 | 11/2010 |
| WO | 2013/102848 | 7/2013 |
| WO | 2013/119332 A2 | 8/2013 |
| WO | WO2013119332 A2 | 8/2013 |
| WO | 2014/144980 | 9/2014 |
| WO | 2014/144980 A1 | 9/2014 |

OTHER PUBLICATIONS

PCT International Search Report and Written Opinion for International Application No. PCT/US2016/031323, Applicant Stryker European Holdings I, LLC, forms PCT/ISA/210, 220, and 237, dated Jul. 25, 2016 (13 pages).

Pyo et al., "Targeted gene disruption of matrix metalloproteinase-9 (Gelatinase B) suppresses development of experimental abdominal aortic aneurysms," J. Clinical Investigation, 105(11), pp. 1641-1649, Jun. 2000.

Walton et al., "Inhibition of prostaglandin E2 synthesis in abdominal aortic aneurysms," Circulation, pp. 48-54, Jul. 6, 1999.

Xu et al., "Sp1 increases expression of cyclooxygenase-2 in hypoxic vascular endothelium," J. Biological Chemistry, 275(32), pp. 24583-24589, Aug. 11, 2000.

PCT International Search Report for International Appln. No. PCT/US2013/000033, Applicant TW Medical Technologies LLC, dated Sep. 8, 2013 (11 pages).

(56) References Cited

OTHER PUBLICATIONS

PCT International Search Report and Written Opinion for International Appln. No. PCT/US2015/032847, Applicant TW Medical Technologies LLC, dated Sep. 3, 2015 (19 pages).
Extended European Search Report dated Apr. 3, 2017 for EP Application No. 15798783.5, Applicant Stryker European Holdings I, LLC, 9 pages.
Notice of Rejection for Japanese Patent Application No. 2016-569451 dated May 20, 2017, Applicant Stryker European Holdings I, LLC, 8 pages.
Notification of Second Office Action dated May 31, 2018 for Chinese application No. 201580027802.4 in Chinese with English language translation provided by Chinese associate, 14 pages.

* cited by examiner

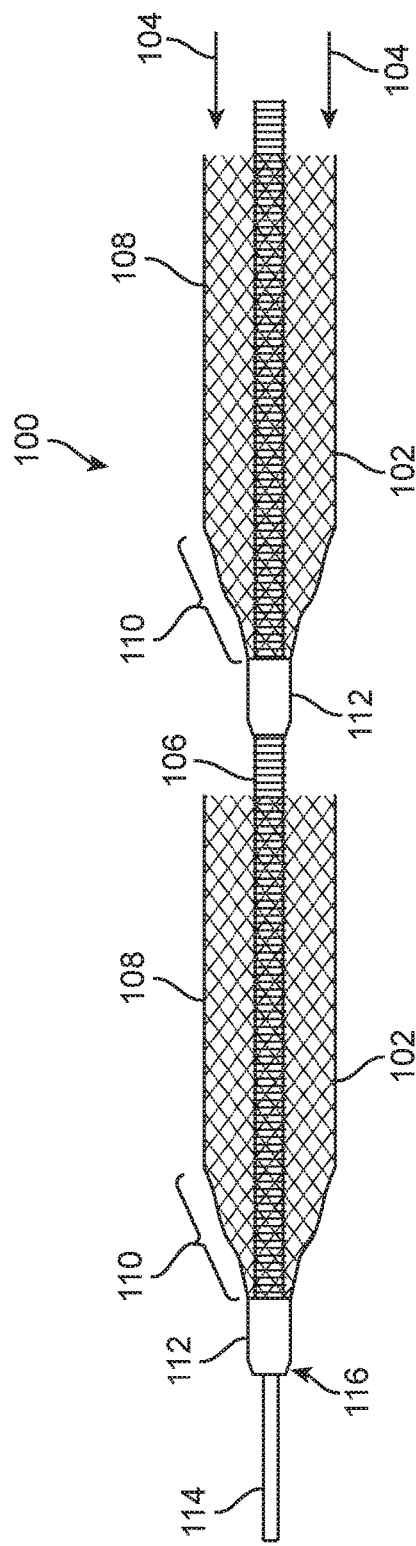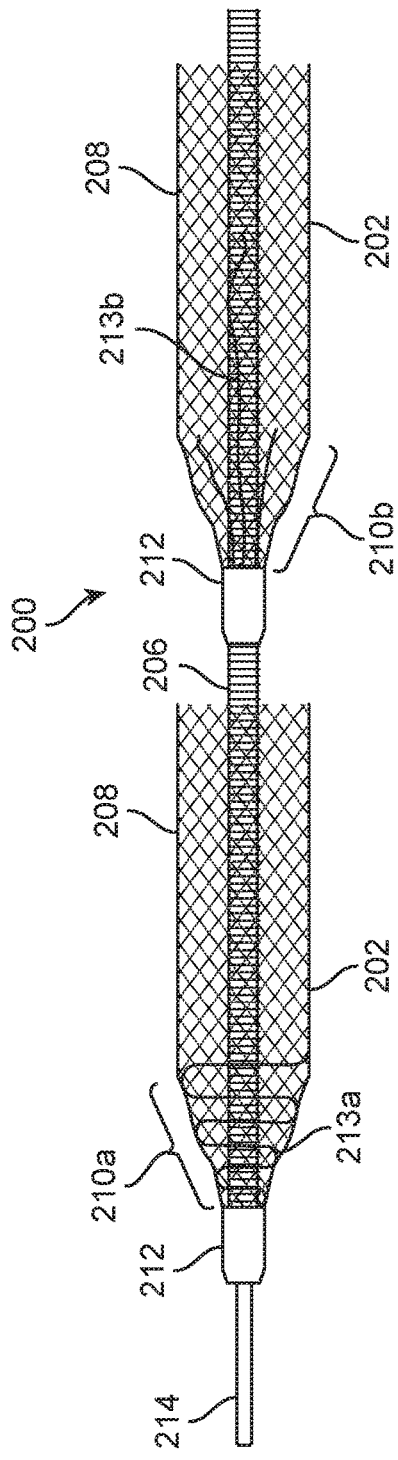
FIG. 1
FIG. 2

VASO-OCCLUSIVE DEVICES

CROSS REFERENCE TO RELATED APPLICATIONS

This patent application claims the benefit of priority under 35 U.S.C. § 119 to U.S. Provisional Application No. 62/159,154, filed on May 8, 2015. This patent application is also related to U.S. Pat. Nos. 9,011,482 and 9,060,777, each filed on May 28, 2014, and each hereby incorporated by reference herein in its entirety.

FIELD

Disclosed and described herein are vaso-occlusive apparatuses (including embolic devices and systems) and method of making and using them. More specifically, disclosed and described herein are pushable and retrievable open-ended vaso-occlusive apparatuses capable of locating with a high precision and including a highly expansive braid for use in vascular and particularly neurovascular applications.

BACKGROUND

An aneurysm is a dilation of a vessel, such as blood vessel, that may pose a risk to a patient's health due from rupture, clotting, or dissecting. For example, rupture of an aneurysm in a patient's brain may cause a stroke, and lead to brain damage and death. Cerebral aneurysms may be detected in a patient, e.g., following seizure or hemorrhage, and may be treated by applying vaso-occlusive devices, such as coils or stents. Coils that may be used to fill or embolize neurological aneurysms are typically made from platinum, and tend to be small coils or springs which can be shaped into a secondary shape of a more complex curve in order to help fill the aneurysm body. Unfortunately, currently used and proposed occlusive devices may sometimes be difficult to position and remove, and can therefore present a risk of migration and resulting harm to the patient, particularly if they become dislodged from the site of insertion.

One type of neurovascular embolization stent coil device that has been proposed includes a central coil (e.g., metal coil) with a woven and/or braid material connected to the device. See, e.g., U.S. Pat. No. 7,749,242 ("the '242 patent"), which describes an expanding vaso-occlusive device including an expandable member attached to a central inner member on both ends of the expandable member but includes an internal "stop" attached to the central inner member. Similarly, U.S. Pat. No. 5,382,259 ("the '259 patent") describes vasoocclusion devices that may include a fibrous, woven or braided covering. Both the '259 patent and the '242 patent require that the woven, expandable outer members be relatively short and limited in expandability, otherwise they are difficult (if not impossible) to push and/or retrieve to/from a cannula. Unfortunately, small (short) coils are often less desirable, as aneurysms with larger mouths are very difficult to treat, particularly with small and relatively thin coils. The coils may slip back out of the aneurysm sack. In addition, procedures using such small, thin, coils may require a longer and more involved procedure. For example, a 7 mm diameter neurological aneurysm may typically be filled with five to seven individual spring shaped coils, resulting in a longer and more complicated procedure than if the number of devices was reduced.

Above-incorporated U.S. Pat. No. 9,011,482 discloses and describes braid-stent coil structures in which an expandable braided portion (which may be very long, e.g., 5 cm and longer) is connected to a pushable/pullable metal coil; the metal coil may provide a pushable core that may be used to position the braided expandable member. In the embodiments described herein, the tubular braided region may be fixed to the metal coil at only a single position, and be of great length and have an expanded diameter that is much larger than the diameter of the push coil, while still allowing the device to be pushed to insert from a catheter and pulled to retrieve into a catheter. Although these apparatuses, devices and methods work surprisingly well, particularly in comparison to prior art devices, there are a number of ways in which they could be improved upon. Towards this end, disclosed and described herein are improved pushable, distally-open devices that may be used to implant (and retrieve/reposition) within a body region, that are both soft and highly expandable.

SUMMARY

Disclosed and described herein are vaso-occlusive devices that include one or more soft and expandable braid on a coil that maybe pushed, with the open distal-facing end forward, for insertion from within an aneurism using a delivery catheter and pulled proximally to retrieve.

Any of the implants (pushable distally-open braids on coils) disclosed and described herein may be configured as previously described, but may be modified as described an illustrated herein. For example, a treatment system including these devices may include a delivery catheter extending from a proximal end to a distal end. The devices may be configured as a vaso-occlusive device within the delivery catheter, wherein the vaso-occlusive device is adapted to be pushed out of, and retrieved back into, the distal end of the delivery catheter. The vaso-occlusive device comprising: an elongate inner member (e.g., coil) having a length and a diameter; and one or more (e.g., a plurality of) distally-open, adjacently arranged outer braided tubular member(s) that are distally pushable out of the delivery catheter. A proximal end of each of the outer braided tubular members may be fixed to the elongate inner member but a distal end of each of the outer braided tubular members is not attached to the elongate inner member. Each of the outer braided tubular members may have a length that is greater than 5 cm, and less than the length, when deployed, of the elongate inner member. Each of the outer braided tubular members may have a collapsed configuration when held within the delivery catheter, and expands to an expanded configuration having a diameter of greater than 1.5 times the diameter of the inner member at a distal end of each of the outer braided tubular members when released from the delivery cannula. Each of the outer braided tubular members may be formed from about 24 to 36 strands (or more, e.g., 24 to 48, 24, 60, etc.) of shape memory material (e.g., Nitinol). Each of the outer braided tubular members may have a braid angle of 35 degrees or less in the collapsed configuration within the delivery catheter. Additional features may include, at the proximal end: an increase in the number of braided filaments (e.g., greater than 24) bound to the proximal end; an increase in the diameters of 1 or more of the braid filaments (relative to the other filaments); selectively add an additional filament(s) after or during braiding to a section near the proximal end (where it attaches to the coil); filaments could be bonded, threated, sutured, tied, etc. to the braid. Any of these modifications may create a stress relief transition between the bonded braid section where the braid is bonded to the coil, and in the adjacent proximal section of the coil.

Alternatively or in addition, a thin metallic or polymeric film may be shrunk, bonded or attached around the transition section between the attachment portion to the coil and the expanded braid region (at the proximal end) to help reinforce the transition section. The film can cover the whole surface area of the braid or a small portion. An adhesive (rigid, elastic or semi elastic) may be added to the braid after the braid is formed on this transition region. Adhesive or reinforcement can placed on the braid in any form, pattern or shape. Alternatively or additionally, the adhesive or reinforcement element can be placed anywhere along the length of the braid to aid in pushability of the braid/coil assembly.

To reduce the distal stiffness of the braid, the distal ends of the braid, when collapsed and expanded configuration around the inner member (coil) the distal end of each braid section can be modified from all the filaments being straight and of similar length. Any of the apparatuses (devices and methods) described herein may include one or more features, as described and illustrated in FIGS. 4-7, to minimize the stiffness of the assembly, e.g., where the proximal end of the braid attaches to the coil member.

In exemplary embodiments of the disclosed inventions, a vaso-occlusion system for occluding an aneurysm includes a delivery catheter having a delivery lumen extending therethrough, a pusher member at least partially extending through the delivery lumen, and a vaso-occlusive device loaded within the delivery lumen, the vaso-occlusive device comprising an expandable braid formed out of a plurality of elongate braid filaments, the elongate braid elements having respective proximal end portions that are formed into a flexible transition section having a proximal end portion attached to a distal end of the pusher member and/or to an elongate central member coupled to, and extending distally of, the pusher member. By way of non-limiting example, in the flexible transition section, the proximal end portions of the elongate braid members may be wound into a helical formation that spirals around the pusher member and/or elongate central member. In one such embodiment, the respective proximal end portions of the elongate braid members are unbraided to form straight filaments prior to being wound into the helical formation. For example, the proximal end portions of the elongate braid members comprising the flexible transition section are heat seat into the helical formation. In some embodiments, the vaso-occlusive device includes an elongate central member (e.g., a coil) to which the flexible transition section is attached. In such embodiments, the proximal end portion of the flexible transition section is preferably fused or otherwise attached to the elongate central member proximate a junction formed with the pusher member. The expandable braid preferably comprises a tubular body portion, wherein the elongate central member may extend through a lumen formed by the tubular body portion, or may extend alongside the tubular body portion, in which case the elongate central member may be attached to the tubular body portion, e.g., by one or more respective elongate braid filaments, at one or more axially spaced attachment locations.

These and additional embodiments, aspects and features of the disclosed inventions are disclosed and described herein.

BRIEF DESCRIPTION OF THE DRAWINGS

A better understanding of the features and advantages of the disclosed inventions will be obtained by reference to the following detailed description that sets forth illustrative embodiments, in which the principles of the invention are utilized, and the accompanying drawings of which:

FIG. 1 depicts an exemplary pushable, distally-open, vaso-occlusive device, including a plurality of braid members adhered to an elongate central coil member, which is pushable through a delivery lumen of a delivery catheter for implantation within a vascular malformation, such as a brain aneurysm.

FIG. 2 depicts one embodiment of a pushable, distally-open, braided vaso-occlusive device attached to an elongate central coil member, according to one embodiment of the disclosed inventions.

DETAILED DESCRIPTION

Figure 3:
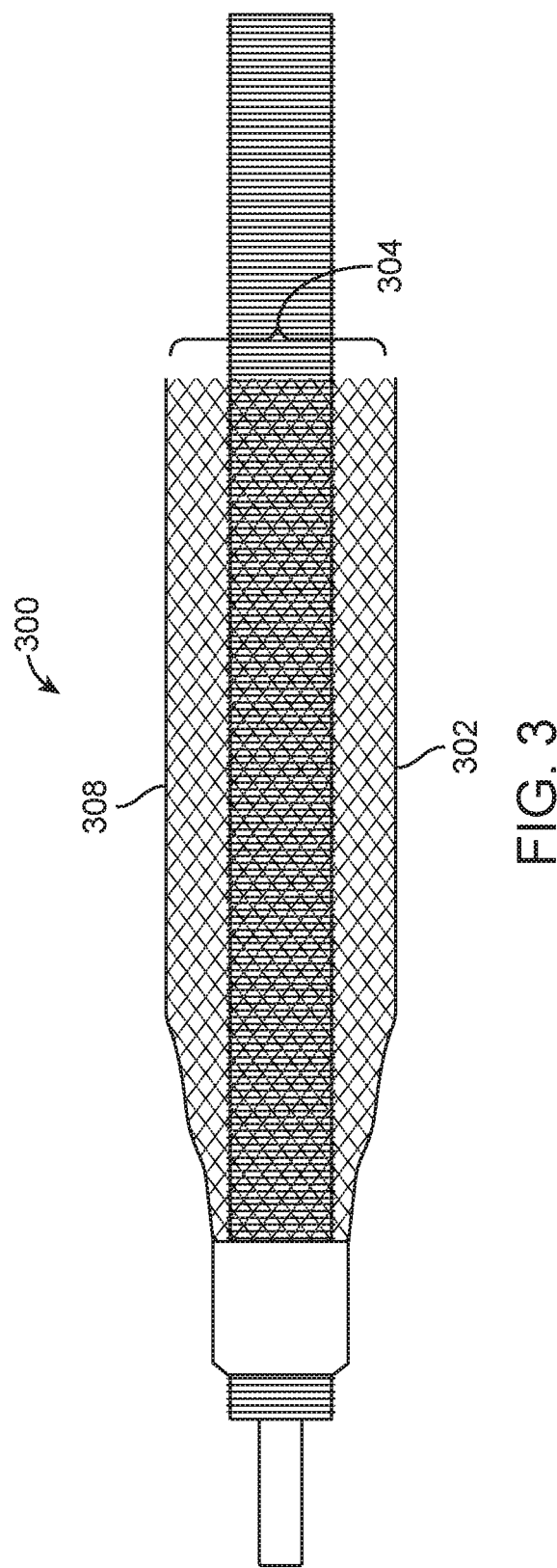
FIG. 3 depicts another embodiment of a pushable, distally-open, braided vaso-occlusive device attached to an elongate central coil member, according to another embodiment of the disclosed inventions.

Terminology used herein is for the purpose of describing particular embodiments only, and is not intended to be limiting of the disclosed inventions—which are defined and limited only by the appended claims, and equivalents thereof. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, terms such as "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the disclosed inventions.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

Although various illustrative embodiments are described above, any of a number of changes may be made to various embodiments without departing from the scope of the disclosed inventions, as defined by the appended claims and equivalents thereof. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

Various embodiments of vaso-occlusive devices having one or more expandable braided portions (e.g., braid 108 in FIG. 1), each braided portion having at least one end (typically a proximal end) bonded to an elongate central member (e.g., coil 106 in FIG. 1) are disclosed and described herein. It should be appreciated that various features and aspects of the disclosed embodiments will also be useful and applicable for braided vaso-occlusive devices that do not have a central member (whether in the form of a coil or otherwise). For example, employing a flexible junction for attaching one end of an expandable braid to a central member as depicted in the embodiments shown in FIGS. 4-7 is advantageous even if the member to which the braid is bonded does not extend beyond (or much beyond) the junction. Nor are the advantages obtained by these embodiments of a flexible joint connecting the braid limited to connections to a coil member.

With reference to FIG. 1, when pushing (indicated by arrows 104) a braided occlusive device 100 through a delivery catheter (not shown), the maximum longitudinal compressive forces on each braid piece 102 will be located at a respective tapered, transition section 110 in which the respective braid 102 transitions from a bonded braid section 112 (bonded to the inner coil member 106, which itself is attached to a pusher wire 114) to a main body portion 108, in which the respective braid 102 is free to expand to its fully expanded heat-treated diameter. Therefore, when friction in the delivery catheter is high while pushing the device 100 therethrough, the respective tapered transition section 110 of each braid member 102 is most likely to be damaged, wrinkle, bunch up and/or otherwise become unstable. Also, the braid in the transition section 110 may take on a "permanent" new shape after being loading into the delivery catheter lumen, which is not conducive for being pushed through (and out) of the delivery catheter.

In accordance with embodiments of the disclosed inventions, design and manufacturing variations and techniques may be employed so that the respective braid transition section 110 is less likely to become damaged when pushing the device through a delivery catheter. Such design and manufacturing variations and techniques may include (i) improving the heat treating process to insure greater memory of the tapered braid shape in the transition section 110; (ii) increasing the number and/or diameters of the braided filaments to add stiffness to the transition section 110; (iii) selectively adding additional filament(s) to the transition section 110 after or during the braiding process, e.g., in which the additional filament(s) is/are bonded, threated, sutured, tied, etc., to the braid to create a stress relief transition between the bonded braid section 112 and expanded braid section 108; (iv) shrinking (e.g., as in shrink-wrap fitting), bonding, or otherwise attaching a reinforcing thin metallic or polymeric film around the transition section 110, wherein the film may cover the whole surface area of the braid section 110, or only a portion thereof; (v) adding a rigid, elastic or semi elastic adhesive to the transition section 110 after the respective braid 102 is formed, wherein the adhesive or reinforcement may be placed on the braid 102 in any form, pattern or shape (see respective elements 213*a* and 213*b* in the embodiment of FIG. 2); additionally or alternatively, the adhesive or reinforcement element can be placed anywhere along the length of the braid to aid in pushability of the braid/coil assembly.

In particular, FIG. 2 depicts an alternative multi-braid vaso-occlusive device 200, constructed according to one embodiment of the disclosed inventions. Similar to the vaso-occlusive 100 shown in FIG. 1, the vaso-occlusive 200 has a plurality of braid members 202, each braid member 202 including a tapered transition section (210a and 210b) in which the respective braid member 202 transitions from a bonded braid section 212 (bonded to the inner coil member 206, which itself is attached to a pusher wire 214) to a main body portion 208, in which the respective braid 202 is free to expand to its fully expanded heat-treated diameter. However, the device 200 differs from device 100, in that the respective braid transition sections 210a and 210b include added adhesive reinforcement to maintain their structural rigidity when loaded into, and pushed through, the delivery lumen of a delivery catheter (not shown).

With reference to a further alternative braided vaso-occlusive device 300 shown in FIG. 3 (only a single braid member 302 is shown, but the device 300 may optionally have additional braid members 302) constructed according to another embodiment of the disclosed inventions, to reduce the distal stiffness of the braid 302 and/or of the open braid filament ends 304, the distal ends of the braid members can be modified, so that rather than having all the members (or "filaments") being straight and of similar length, some of the filaments in the braid construction would be shorter than others to reduce the numbers of filaments at the braid distal end. For example 10%, 20, 30%, 40%, 50%, 60% or 70% of the filaments would be shorter than the longest filament. In a preferred embodiment, the shorter elements would be 3-10 mm shorter than the longest element. Alternatively or in addition, the braid member filament ends 304 could be heat set to have a relaxed configuration flare outwards or inwards in a radial fashion. Such a heat shape would reduce the stiffness of the braid member filament ends 304. Further alternatively or additionally, the braid member filament ends 304 could be flipped/folded (everting or inverting) back onto the main body portion 308 of the braid 302.

Figure 4:
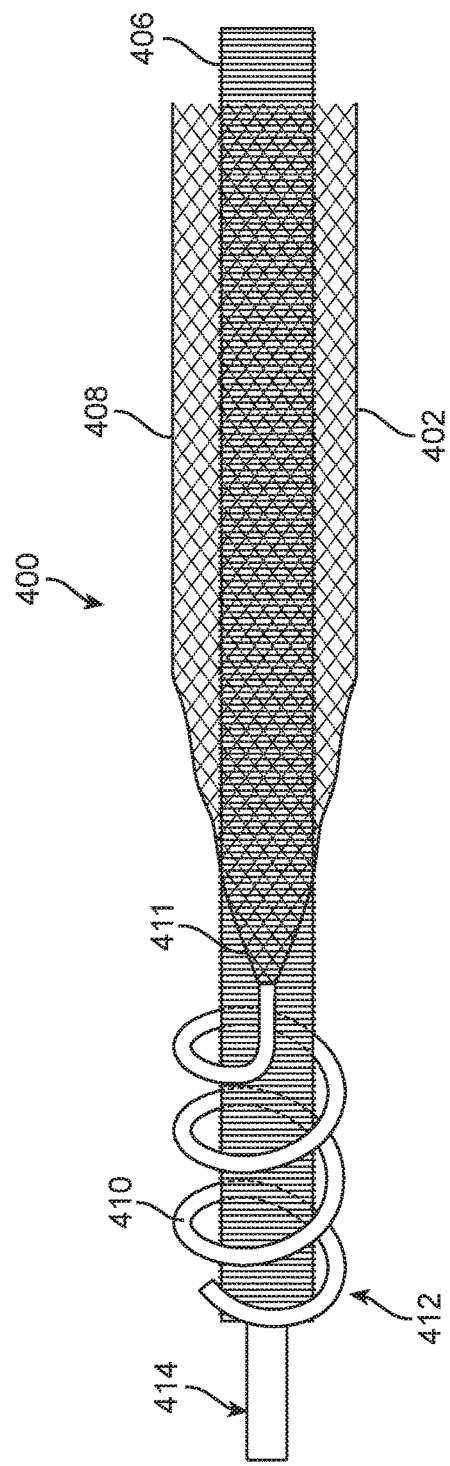
FIG. 4 depicts yet another embodiment of a pushable, distally-open, braided vaso-occlusive device attached to an elongate central coil member, according to yet another embodiment of the disclosed inventions.

In accordance with another aspect of the disclosed inventions, it may be preferable to minimize the stiffness of the vaso-occlusive assembly, as shown in the further alternative braided vaso-occlusive device 400 depicted in FIG. 4. In particular, the device 400 includes at least a first braid member 402, wherein a proximal end portion 411 of the braid 402 is attached to an inner coil member 406 using a flexible junction 410. Specifically, as shown in FIG. 4, the respective braid filaments or wires forming the braid 402 are wrapped into a helical, coil like structure 410 that extends proximally from the main body portion 408 of the braid 402, and is fused or otherwise attached to the inner coil member 406 proximate a junction 412 formed between the coil 406 and a pusher member 414. The proximal braid portion 410 is formed and optionally heat set into a helical shape. To reduce the assembly diameter created by the helical braid structure 410 being wrapped around the coil 406, the ends of the braid filaments may be unraveled (unbraided) to form straight filaments and then helically wound, as depicted in FIG. 5.

Figure 5:
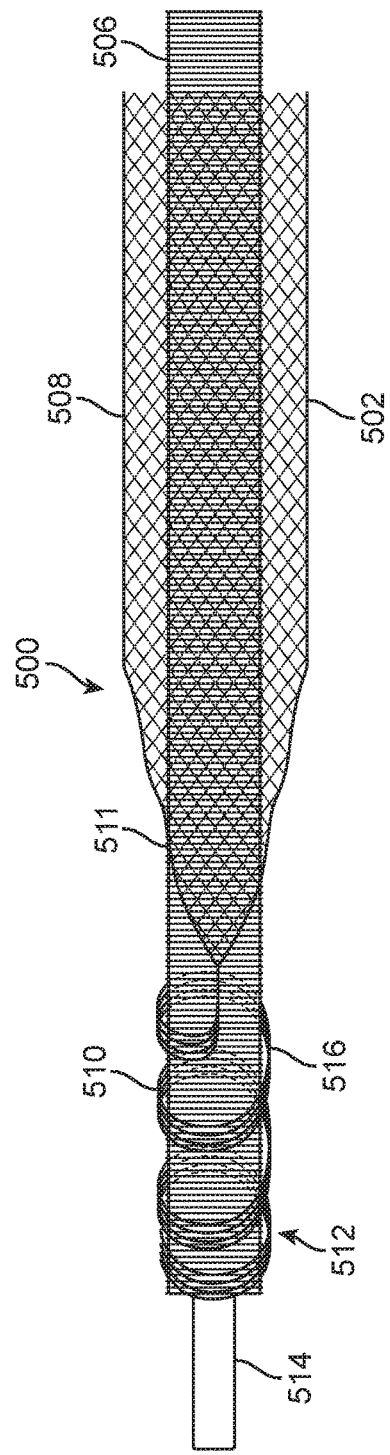
FIG. 5 depicts still another embodiment of a pushable, distally-open, braided vaso-occlusive device attached to an elongate central coil member, according to yet another embodiment of the disclosed inventions.

In particular, FIG. 5 depicts a further alternative braided vaso-occlusive device 500, including at least a first braid member 502, wherein the individual braid filaments 516 in a proximal end portion 511 of the braid 502 are unraveled (unbraided) to form straight filaments, which are then wound into the depicted helical formation, and attached to the inner coil member 506 proximate a junction 512 formed between the coil 506 and a pusher member 514. The proximal braid portion 510 is formed and optionally heat set into a helical shape.

In the embodiments shown in FIG. 4 and FIG. 5, the respective braid member 402/502 is concentrically loaded around the respective central coil member 406/506. Alternatively, the main braid section 402/502, along with the respective proximal (helically wound) flexible transition section 410/510 may be concentrically placed around the coil 406/506, where the proximal portion of the respective braid member 402/502 is oriented so the transistion section 410/510 is twisted around the center coil 406/506 in either a clockwise or counterclockwise orientation. After the proximal portion of the respective braids 402/502 are formed into the twisted, helical transition sections 410/510, the proximal end of the respective transition sections may be secured to the respective coil 406/506. The resulting, twisted helical-like braid structures may include some unraveled filaments, such as depicted in FIG. 5.

Figure 6A:
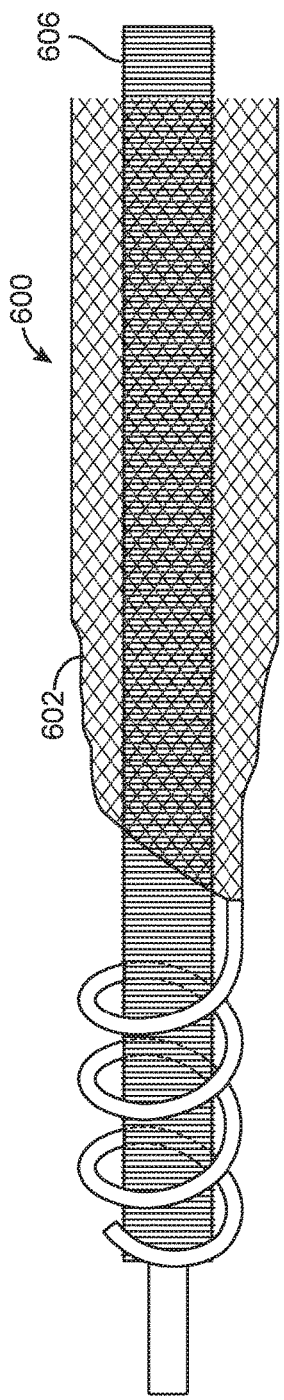
FIG. 6A is a side view of yet another embodiment of a pushable, distally-open, braided vaso-occlusive device attached to an elongate central coil member, according to yet another embodiment of the disclosed inventions.
Figure 6B:
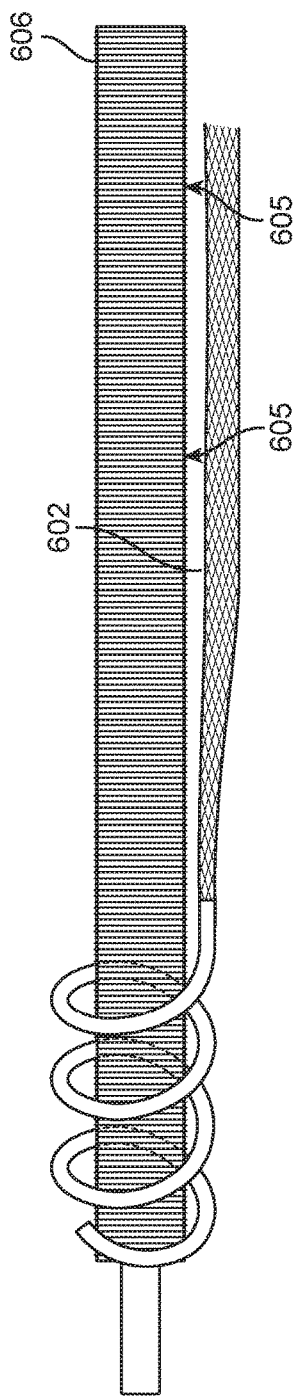
FIG. 6B is a top view of the braided vaso-occlusive device of FIG. 6A.
Figure 6C:
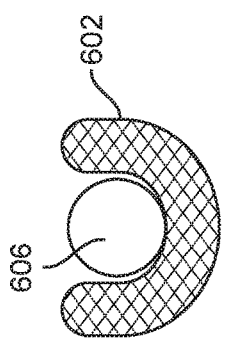
FIG. 6C is an end-view of the braided vaso-occlusive device of FIG. 6A.

Alternatively, a braid member 602 of the further alternative vaso-occlusive device 600 depicted in FIGS. 6A, 6B and 6C is positioned adjacent to, and mostly parallel with, an elongate central coil 606, and not in a concentric arrangement. Optionally, and as shown in the braid in FIG. 6B may be attached to the coil at one or more axially spaced attachment locations 605 by securing one or more braid filaments that are most proximal to the side of the coil 606, through an adhesive, suture looped around filaments around coil 606 or other means or combination thereof.

Figure 7:
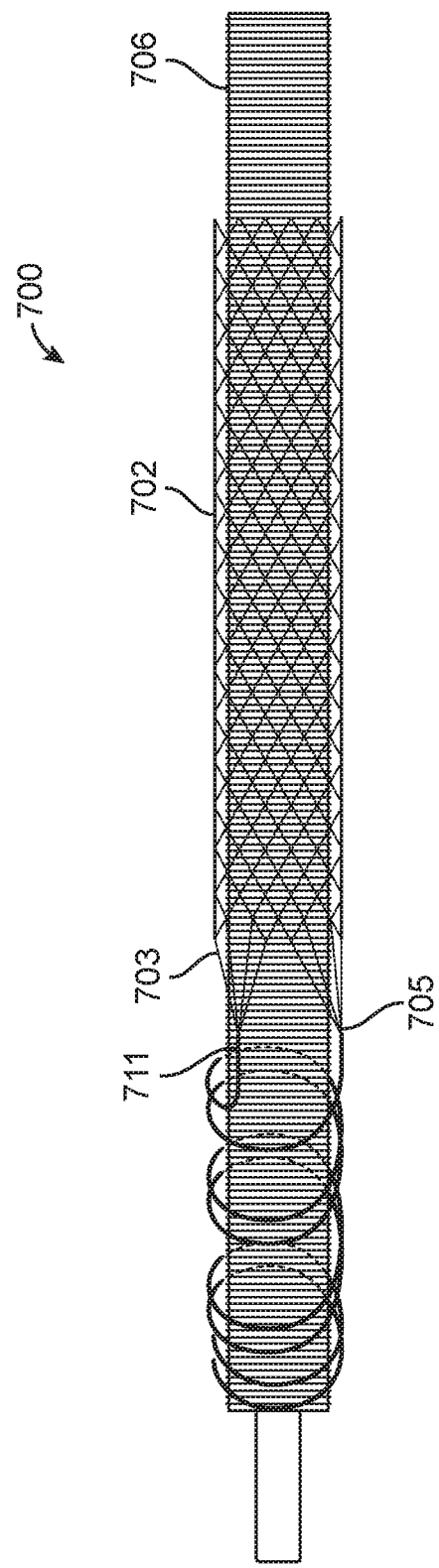
FIG. 7 depicts still another embodiment of a pushable, distally-open, braided vaso-occlusive device attached to an elongate central coil member, according to yet another embodiment of the disclosed inventions.

Further alternatively, as shown in the vaso-occlusive device 700 of FIG. 7, the proximal end 711 of the braid 702 may be split into two separate bunches of filaments, bunch 703 and bunch 705. Both bunches are formed into their own helical shape and placed around the coil element 706. In the configuration shown in FIG. 7, the maximum diameter of the device 700 should be smaller than the deice 300 shown in FIG. 3 assuming the braid construction (number of filaments/ends, size of filament, braid angle . . . etc.) and the coil construction are otherwise the same.

Still further alternatively, the embodiment shown in FIG. 3 could have three or more separate bunches of filaments, wherein each bunch of filaments could be unraveled or unbraided so as to lie in parallel to each other when formed into a coil, further reducing its effective assembly diameter.

The disclosed and described examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description and the accompanying figures.

What is claimed is:

1. A vaso-occlusion system for occluding an aneurysm, comprising:
   a delivery catheter having a delivery lumen extending therethrough;
   a pusher member at least partially extending through the delivery lumen; and
   a vaso-occlusive device loaded within the delivery lumen, the vaso-occlusive device comprising an expandable braid formed out of a plurality of elongate braid filaments, the elongate braid filaments having respective proximal end portions that are formed into a flexible transition section having a proximal end portion attached to a distal end of the pusher member and/or to an elongate central member coupled to, and extending distally of, the pusher member,
   wherein in the flexible transition section, the proximal end portions of the elongate braid filaments are unbraided to form straight filaments that are wound into a helical formation that spirals around the pusher member and/or elongate central member.

2. The vaso-occlusion system of claim 1, wherein the proximal end portions of the elongate braid filaments comprising the flexible transition section are heat seat into the helical formation.

3. The vaso-occlusion system of claim 1, the vaso-occlusive device comprising the elongate central member to which the flexible transition section is attached.

4. The vaso-occlusion system of claim 3, wherein the elongate central member comprises a coil.

5. The vaso-occlusion system of claim 3, wherein the proximal end portion of the flexible transition section is fused or otherwise attached to the elongate central member proximate a junction formed with the pusher member.

6. The vaso-occlusion system of claim 3, wherein the expandable braid comprises a tubular body portion.

7. The vaso-occlusion system of claim 6, wherein the elongate central member extends through a lumen formed by the tubular body portion.

8. A vaso-occlusion system for occluding an aneurysm, comprising:
   a delivery catheter having a delivery lumen extending therethrough;
   a pusher member at least partially extending through the delivery lumen; and
   a vaso-occlusive device loaded within the delivery lumen, the vaso-occlusive device comprising an elongate central member coupled to, and extending distally of, the pusher member, and an expandable braid formed out of a plurality of elongate braid filaments having respective proximal end portions that are formed into a flexible transition section having a proximal end portion attached to a distal end of the elongate central member,
   wherein the expandable braid comprises a tubular body portion, and
   wherein the elongate central member extends alongside the tubular body portion.

9. The vaso-occlusion system of claim 8, wherein the elongate central member is attached to the tubular body portion at one or more axially spaced attachment locations.

10. The vaso-occlusion system of claim 9, wherein, at each attachment location, the elongate central member is attached to the tubular body portion by one or more respective elongate braid filaments.

11. A vaso-occlusive device, comprising:
   an elongate central support member; and
   an expandable braid formed out of a plurality of elongate braid filaments, the elongate braid filaments having respective proximal end portions that are formed into a flexible transition section having a proximal end portion attached to the elongate central member,
   wherein in the flexible transition section, the proximal end portions of the elongate braid filaments are unbraided to form straight filaments that are wound into a helical formation that spirals around the elongate central member.

12. The vaso-occlusive device of claim 11, wherein the proximal end portions of the elongate braid filaments comprising the flexible transition section are heat seat into the helical formation.

13. The vaso-occlusive device of claim 11, wherein the elongate central member comprises a coil.

14. The vaso-occlusive device of claim 11, wherein the proximal end portion of the flexible transition section is fused or otherwise attached to the elongate central member proximate a junction formed with a pusher member.

15. The vaso-occlusive device of claim 11, wherein the expandable braid comprises a tubular body portion, and wherein the elongate central member extends through a lumen formed by the tubular body portion.

16. The vaso-occlusive device of claim 11, wherein the elongate central member extends alongside the tubular body portion, and wherein the elongate central member is attached to the tubular body portion by one or more respective elongate braid filaments at each of one or more axially spaced attachment locations.

* * * * *